(12) United States Patent
Tets et al.

(10) Patent No.: US 10,253,037 B2
(45) Date of Patent: Apr. 9, 2019

(54) DRUG WITH ANTIVIRAL ACTIVITY (VARIANTS)

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Konstantin Andreevich Krasnov, St. Petersburg (RU)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 0 days.

(21) Appl. No.: 15/564,009

(22) PCT Filed: Apr. 6, 2016

(86) PCT No.: PCT/RU2016/000197
§ 371 (c)(1),
(2) Date: Oct. 3, 2017

(87) PCT Pub. No.: WO2016/159836
PCT Pub. Date: Oct. 6, 2016

(65) Prior Publication Data
US 2018/0134723 A1    May 17, 2018

(30) Foreign Application Priority Data

Apr. 3, 2015    (RU) ............................... 2015113254

(51) Int. Cl.
| | | |
|---|---|---|
| *A61K 31/519* | (2006.01) | |
| *C07D 491/147* | (2006.01) | |
| *A61P 31/20* | (2006.01) | |
| *A61P 31/18* | (2006.01) | |
| *A61K 31/513* | (2006.01) | |
| *A61K 31/7072* | (2006.01) | |

(52) U.S. Cl.
CPC ........ *C07D 491/147* (2013.01); *A61K 31/513* (2013.01); *A61K 31/519* (2013.01); *A61K 31/7072* (2013.01); *A61P 31/18* (2018.01); *A61P 31/20* (2018.01); *A61K 2300/00* (2013.01)

(58) Field of Classification Search
CPC ........................... C07D 491/147; A61K 31/519
See application file for complete search history.

(56) References Cited

U.S. PATENT DOCUMENTS 4,578,380 A    3/1986    Satzinger et al.

FOREIGN PATENT DOCUMENTS

| EP | 0237289 A2 | 9/1987 |
| JP | H0381276 A | 4/1991 |
| RU | 2188201 C2 | 8/2002 |
| RU | 2246496 C1 | 2/2005 |

OTHER PUBLICATIONS

Viral Infection Treatment drugs, retrieved from https://www.omicsonline.org/scholarly/viral-infection-treatment-drugs-journals-articles-ppts-list.php on Jun. 13, 2018 (Year: 2018).*
O'Neill, The diversity of retroviral diseases of the immune system, Immunology and Cell Biology, 1992, vol. 70, p. 193-199. (Year: 1992).*
Machine translation of RU Pub. No. 2188201, Ashkinazi et al, pu. Aug. 27, 2002, p. 1-4. (Year: 2002).*
International Search Report Issued in PCT/RU2016/000197 dated Sep. 8, 2016 and English Translation Thereof; 4 pages.
International Preliminary Report on Patentability issued by the International Searching Authority in International Application No. PCT/RU2016/000197 dated Oct. 3, 2017, 6 pages total.
Written Opinion issued by the International Searching Authority in International Application No. PCT/RU2016/000197 dated Sep. 8, 2016, 11 pages total.

* cited by examiner

*Primary Examiner* — Rebecca L Anderson
*Assistant Examiner* — Karen Cheng
(74) *Attorney, Agent, or Firm* — Troutman Sanders LLP

(57) ABSTRACT

The invention relates to the field of organic chemistry and medicine, and more particularly to synthetic substances of the pyrimidine series, namely 2-chloro-5-phenyl-5H-pyrimido[5',4':5,6]pyrano[2,3-d]pyrimidine-4-ol derivatives, having antiviral activity. Claimed are a drug with antiviral activity against HIV infection and hepatitis B virus, containing 2-chloro-5-phenyl-5H-pyrimido[5',4':5,6]pyrano[2,3-d]pyrimidine-4-ol derivatives of the general formula shown, where: X is selected from the group: H, $NO_2$, Hal, OMe; R1 is selected from the group: Cl, OH; and R2 is selected from the group: Cl, SH, OH; and a drug with antiviral activity against HIV infection, containing a 2-chloro-5-phenyl-5H-pyrimido[5',4':5,6]pyrano[2,3-d]pyrimidine-4-ol derivative of the general formula shown, where: X is selected from the group: H, $NO_2$, Hal, OMe; R1 is selected from the group: Cl, OH; and R2 is selected from the group: Cl, SH, OH in combination with a reverse transcriptase inhibitor selected from Retrovir, or in combination with a protease inhibitor selected from Lopinavir, in an effective amount. The result is an effective drug with antiviral activity.

26 Claims, No Drawings

DRUG WITH ANTIVIRAL ACTIVITY (VARIANTS)

CROSS-REFERENCE TO RELATED APPLICATIONS

This application is a U.S. National Phase of International Patent Application No. PCT/RU2016/000197, filed on Apr. 6, 2016, which published as WO 2016/159836 A1 on Oct. 6, 2016, and claims priority to Russian Patent Application No. 2015113254, filed on Apr. 3, 2015, all of which are herein incorporated by reference in their entirety.

TECHNICAL FIELD

The invention relates to the field of organic chemistry and medicine, and more particularly to synthetic substances of the pyrimidine series, namely 2-chloro-5-phenyl-5H-pyrimido[5',4':5,6]pyrano[2,3-d]pyrimidine-4-ol derivatives, having antiviral activity.

The invention can be used to treat diseases caused by immunodeficiency viruses and other retroviruses, hepatitis B viruses, and also for similar purposes in veterinary medicine. The subject agent can be used both in an individual form and in combination with other drugs and pharmaceutical additives.

BACKGROUND ART

It is commonly known that pyrimidine derivatives have a pronounced biological activity and participate in the vital processes of organisms. Pyrimidine derivatives are nucleic bases (uracil, thymine, cytosine), vitamins (thiamine, phosphothiamine), coenzymes (cocarboxylase), growth regulators (orotic acid), etc. [Data for Biochemical Research (3rd ed), R. M. C. Dawson, D. C. Elliott, W. H. Elliott, K. M. Jones (Clarendon Press, 1986].

Of particular interest are systems in which the pyrimidine ring is annelated by other heterocycles. These include purines that are part of nucleic acids (adenine, guanine), folic acid, ATF, pterins, flavins, many other natural substances and their synthetic analogues.

From synthetic derivatives of pyrimidine, substituted barbituric and 2-thiobarbituric acids are among the most widely used in medicine. Data on the biological activity of various derivatives of 5-ylidenebarbituric acids are summarized in the review [2-Sans R G, Chosas M G//Pharmazie, 1988, Bd 43, N 12, S. 827-829], where the anticonvulsant, antimicrobial, antispasmodic, antipyretic, and anticancer effect of these substances is noted.

High biological activity was also found in annelated pyrimidine derivatives, for example, in pyrazolo[3,4-d]pyrimidines obtained by condensation of 6-hydrazinouracils with iso(thio)cyanates [3-Naka T., Nagaoka A., Furukawa Y., EPO application No. 237289 (1987)], 5-deazaflavines [4-Yoneda F., Sasaki T., Japanese Patent, M cl.C 07D 471/04, No. 03 81276, filed on Aug. 24, 1989 (89/218146), published on May 4, 1991], derivatives of pyrrolo[2,3-d]pyrimidines [5-Quijano M L, Nogueras M., Melguizo M., Alvarez de Cienfuegos G., Melgarejo M., Sanches A.// Nucleosides & Nucleotides, 1989, Vol. 8, N 8, P. 1519-1528], pyrano[2,3-d]pyrimidines [6-Ahluwalia V. K., Batla R., Khurana A., Kumar R.//Indian J. Chem., 1990, Vol. 29B, No. 12, P. 1141] and pyrimido[4,5-c]pyridazines [7-Billings B. K., Wagner J. A., Cook F. D., Castle R. N.//J. Heterocycl. Chem., 1975, Vol. 12, N 6, P. 1221-1224]. The listed compounds possess pesticide, antitumor, antimicrobial, immunosuppressive, nootropic, antihypertensive and antiallergic action.

The above materials indicate the prospect of finding new pharmaceuticals among the pyrimidine derivatives.

At the same time, only a few examples of the formation of a pyrano[2,3-d:6,5-d'] dipyrimidine system are known, in particular, when barbituric acids react with 3-acylchromones [8—Eiden F., Schikorr W.//Arch. Pharm., 1972, Bd 305, N 3, S. 187-193] [9—Stone K. M., Wittington W. L., Treatment of genital gerpes, Rev. of Infect. Dis., 1990, 12, Supl. 6, P.610-619].

There is no information on their biological activity. As noted above, compounds containing a pyrimidinedione fragment have a variety of biological activities. However, the effectiveness of many of the substances studied is not high enough, many of them are toxic and have side effects. In addition, bacteria, viruses and tumor cells very rapidly become resistant to existing drugs [10-Stone K M, Wittington W L, Treatment of genital gerpes, Rev. Of Infect. Dis., 1990, 12, Supl. 6, P.610-619].

A preparation known as Raltegravir has been selected as the prototype of the invention; it is an integrase inhibitor, N-(2-(4-(4-fluorobenzylcarbamoyl)-5-hydroxy-1-methyl-6-oxo-1,6-dihydropyrimidin-2-yl) propan-2-yl) of the following general formula:

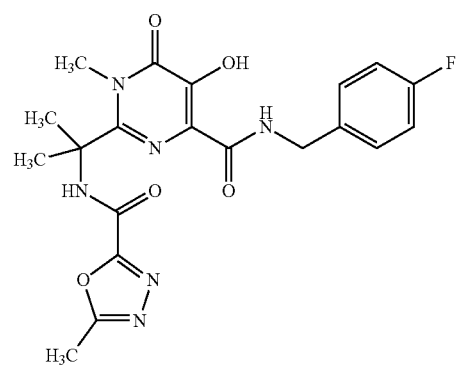

(world wide web at accessdata.fda.gov/drugsatfda_docs/label/2011/022145s0181b1.pdf).

The drug inhibits the catalytic activity of HIV integrase, an enzyme involved in viral replication. Inhibition of integrase prevents covalent introduction of the HIV genome into the genome of the host cell in the early stages of infection. Disadvantages of the prototype are associated with the rapidly emerging resistance of viruses to this drug, which causes its low efficiency.

SUMMARY OF THE INVENTION

The object of the present invention is to provide an effective medicament with antiviral activity.

According to the invention in variant 1, the task is achieved by the synthesis of a medicament with antiviral activity against HIV infection and hepatitis B virus, which is composed of derivatives of 2-chloro-5-phenyl-5H-pyrimido [5',4':5,6]pyrano[2,3-d] pyrimidin-4-ol of the following general formula:

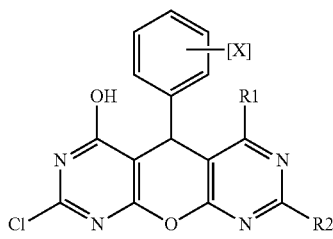

where: X is selected from the group: H, NO$_2$, Hal, OMe;
R1 is selected from the group: Cl, OH;
R2 is selected from the group: Cl, SH, OH;

According to the invention in variant 2, the task is achieved by the synthesis of a medicament with antiviral activity against HIV infection, which contains a derivative of 2-chloro-5-phenyl-5H-pyrimido[5',4':5,6]pyrano[2,3-d]pyrimidin-4-ol of the following general formula:

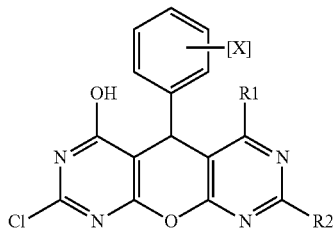

where: X is selected from the group: H, NO$_2$, Hal, OMe;
R1 is selected from the group: Cl, OH;
R2 is selected from the group: Cl, SH, OH Together with a reverse transcriptase inhibitor selected from Retrovir, or in combination with a protease inhibitor selected from Lopinavir, in an effective amount.

The invention applies to all spatial isomers of the subject compounds and all of their tautomeric forms, and also salts.

The applicant has not found any sources of information containing data on technical solutions identical to the claimed invention, which enables to conclude that the claimed invention conforms to the criterion "Novelty" (N).

The applicant has not found any sources of information containing data on the effect of the distinctive features of the invention on the technical result achieved due to their implementation. This, according to the applicant, demonstrates the compliance of this technical solution with the condition of patentability "Inventive Step" ("IS").

BRIEF DESCRIPTION OF DRAWINGS

In the following, the invention is explained with a detailed description of examples of its implementation without reference to the drawings.

Preferred Embodiment

To solve the problem, the derivatives of the subject substance listed in Table 1 are most preferred.

Synthesis of the Subject Medicinal Product

Derivatives 1-7 of the subject substance are synthesized in 2 stages in accordance with Diagram 1.

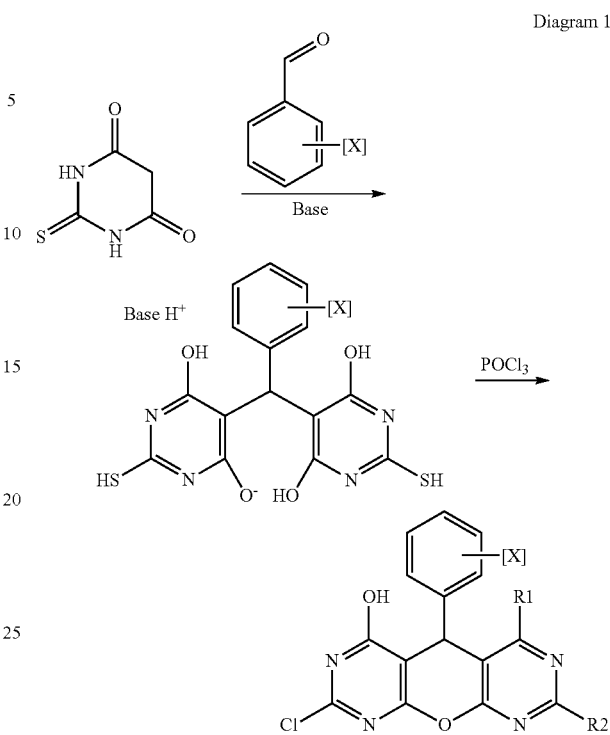

Diagram 1

To obtain the subject substances, intermediates are first synthesized, which are the salts of the derivatives of bis-[5-(2-sulfhydryl-4,6-dihydroxyhexahydropyrimido)]phenylmethane from the corresponding aromatic aldehydes and 2-thiobarbituric acid in the presence of the base (triethylamine or pyridine). Then, the intermediate compounds are treated with phosphorus oxychloride to synthesize the subject substances.

The subject substance is prepared as follows.

To obtain the derivative, 14.4 g (0.1 mole) of 2-thiobarbituric acid are placed in a 500 ml flask, 150 ml of water are added and the mixture is heated to 90-95° C. Then, 5.01 (0.05 mol) of triethylamine in 7 ml of alcohol is added to the hot solution while stirring, and the mixture is heated for an additional 1 minute until complete dissolution. After that the solution is removed from the heater and a solution of 7.55 g (0.05 mol) of 4-nitrobenzaldehyde in 25-30 ml of hot alcohol is added by pouring. The reaction mixture is stirred without heating for 5 minutes and left at 15-20° C. for 3-4 hours. The precipitated crystalline deposit is filtered off, flushed out with a small amount of water and air dried to a constant weight. 24 g of an intermediate are obtained, which is triethylammonium salt of bis-[5-(2-sulfhydryl-4,6-dihydroxyhexahydropyrimido)]4-nitrophenylmethane in the form of a cream-coloured crystalline powder, T of dec. 240° C.

Then 100 ml of phosphorus oxychloride are placed into a 200 ml flask, heated to boiling, and 10 g of the above intermediate (triethylammonium bis[5-(2-sulfhydryl-4,6-dihydroxyhexahydropyrimido)]-(4-nitrophenyl)methane) are added while stirring, and the stirring is continued with vigorous reflux for 30-50 minutes until the precipitate is completely dissolved, after which it is boiled for another 1 hour. After that, the reaction mixture is cooled to room temperature and with vigorous stirring, and then poured into 350 g of crushed ice. The rate of addition of the mixture is adjusted so that the temperature of the mass is no higher than 15° C. After the addition of the whole mixture, the stirring of the mass is continued, gradually bringing it to the temperature of 20° C., and when the specified temperature is reached, another 50 g of ice are added to the mixture, keeping the temperature within 20-35° C. After completion of the exothermic reaction, the mixture is diluted with water to the final volume of 1 L, the precipitated white deposit is filtered and flushed out with water until a slightly acidic flush reaction (pH 4-5). Next, the crude deposit is transferred to a flask, 200 ml of water and 5 g of tris-hydroxymethyl-aminomethane (TRIS) are added and mixed without heating until the deposit is completely dissolved. The resulting solution is filtered to remove any foreign particles. 100 ml of a 1% aqueous acetic acid solution are added to the filtrate to pH 7 and held for 30 minutes, and the precipitated deposit is separated and discarded. 100 ml of a 1% acetic acid solution are added to the resulting filtrate to pH 5 and the mixture is held for 1 hour, the formed deposit is filtered, flushed out with an aqueous solution of 0.1% acetic acid, then flushed out with pure water and dried in a vacuum desiccator over KOH at a temperature of up to 30° C. 3.5 g of derivative 1 of the subject substance are obtained in the form of a glassy product of brown color. The yield is 40% of the theoretical value.

Note. By the same procedure, the derivatives 5, 6 and 7 are obtained using the corresponding aldehydes (benzaldehyde, 3-chlorobenzaldehyde and 4-methoxyb enzaldehyde). The yield of the products is indicated in Table 2, the characteristics and the elemental analysis data can be found in Tables 3 and 4.

To prepare a mixture of derivatives 1, 2 and 3, 100 ml of phosphorus oxychloride are placed into a 200 ml flask, and heated to boiling. Then 10 g of the intermediate obtained above (salts of bis[5-(2-sulfhydryl-4,6-dihydroxyhexahydropyrimido)]-(4-nitrophenyl)methane) are added to the boiling liquid while stirring, and the stirring is continued with vigorous boiling for 30-50 minutes until the deposit is completely dissolved, after which it is boiled for another 1 hour. After that, the reaction mixture is cooled to room temperature and with vigorous stirring, and then poured into 350 g of crushed ice. The rate of addition of the mixture is adjusted so that the temperature of the mass is no higher than 15° C. After the addition of the whole mixture, the stirring of the mass is continued, gradually bringing it to the temperature of 20° C., and when the specified temperature is reached, another 50 g of ice are added to the mixture, keeping the temperature within 20-35° C. After completion of the exothermic reaction, the mixture is diluted with water to the final volume of 1 liter. The precipitated white deposit is filtered and flushed out with water until a slightly acidic flush reaction (pH 4-5). Next, the crude deposit is transferred to a flask, 200 ml of water and 5 g of tris-hydroxymethyl-aminomethane (TRIS) are added and mixed without heating until the deposit is completely dissolved and a solution with a pH of 8-9 is obtained. The resulting solution is diluted with water to the final volume of 400 ml and filtered to remove any foreign particles. Then 50 ml of an aqueous solution containing 5 ml of acetic acid are added slowly to the resulting filtrate while stirring to reach pH 3. The precipitated solid residue is held for 30 minutes and filtered, the filter cake is flushed out thoroughly with an aqueous solution of 0.1% acetic acid, then flushed out with pure water and air dried at a temperature not exceeding 40° C. After drying, 6 g of a glassy brown product is obtained, which is a mixture of derivatives 1, 2 and 3 of the subject substance in a ratio (%) of 40:30:20, respectively. The total yield is about 80% of the theoretical value.

To obtain the desired product, namely 2-chloro-8-sulfhydryl-5-(4-nitrophenyl)-5H-pyrimido [5',4':5,6]pyrano[2,3-d]pyrimidine-4.6-diol (derivative 2), 100 ml of phosphorus oxychloride are placed into a 200 ml flask and heated to boiling. Then 10 g of the intermediate obtained above (salts of bis[5-(2-sulfhydryl-4,6-dihydroxyhexahydropyrimido)]-(4-nitrophenyl)methane) are added to the boiling liquid while stirring, and the stirring is continued with vigorous boiling for 30-50 minutes until the deposit is completely dissolved. After that, the reaction mixture is cooled to room temperature and portionwise poured into 250 g of crushed ice with vigorous stirring, adjusting the addition rate of the mixture so that the final material temperature is 50-60° C. After completion of the exothermic reaction, the residue is filtered through a paper filter and thoroughly flushed out with water. Next, the crude residue is transferred to a flask and dissolved in 200 ml of water with the addition of 5-6 ml of 25% ammonia. The resulting solution is filtered to remove foreign particles and the filtrate is acidified with an aqueous solution of 5% acetic acid to pH 5. The precipitated residue is separated and discarded, and the filtrate is acidified with HCl to pH 1 and held for 1 hour at 20° C. The precipitated residue is filtered, flushed out with water and dried in a vacuum desiccator over KOH at a temperature of up to 30° C. After drying, 1.35 g of derivative 2 is obtained in the form of a light yellow crystalline powder. The yield is 19% of the theoretical value.

To obtain the desired product, namely 2,6,8-trichloro-5-(4-nitrophenyl)-5H-pyrimido [5', 4':5,6] pyrano [2,3-d] pyrimidin-4-ol (derivative 3), 100 ml of phosphorus oxychloride are placed into a 200 ml flask and heated to boiling. Then 3 g of the intermediate obtained above (salts of bis[5-(2-sulfhydryl-4,6-dihydroxyhexahydropyrimido)]-(4-nitrophenyl)methane) are added to the boiling liquid while stirring, and the stirring is continued with vigorous boiling for 2 hours. After this, at least 70 ml of phosphorus oxychloride are distilled from the mixture in a vacuum at a bath temperature of up to 90° C. and the residue is cooled to room temperature. The reaction mixture is then portionwise poured into 150 g of crushed ice with vigorous stirring, adjusting the addition rate of the mixture so that the mass temperature does not exceed 15° C. After completion of the exothermic reaction, the residue is filtered through a paper filter and thoroughly flushed out with water. Next, the crude residue is transferred to a flask, 100 ml of water and 2 g of tris-hydroxymethylaminomethane (TRIS) are added, and stirred without heating until the residue is completely dissolved and a solution with a pH of 8-9 is obtained. The resulting solution is filtered to remove foreign particles and the filtrate is acidified with an aqueous solution of 1% acetic acid to pH 7. The formed residue is filtered, flushed out thoroughly with water and dried in a vacuum desiccator over KOH at a temperature of up to 30° C. 0.56 g of derivative 3 of the subject substance are obtained in the form of a glassy product of light brown color. The yield is 27% of the theoretical value.

To obtain the desired product, namely 2-chloro-8-sulfhydryl-5-(4-nitrophenyl)-5H-pyrimido [5',4':5,6]pyrano[2,3-d]pyrimidine-4,6,8-triol (derivative 4), 100 ml of phosphorus oxychloride are placed into a 200 ml flask and heated to boiling. Then 10 g of the intermediate obtained above (salts of bis[5-(2-sulfhydryl-4,6-dihydroxyhexahydropyrimido)]-(4-nitrophenyl)methane) are added to the boiling liquid while stirring, and the stirring is continued with vigorous boiling for 30-50 minutes until the deposit is completely dissolved. After that, the reaction mixture is cooled to room temperature and portionwise poured into 250 g of crushed ice with vigorous stirring, adjusting the addition rate of the mixture so that the final material temperature was 50-60° C. After completion of the exothermic reaction, the mixture is stirred at 50° C. for 8 hours. The mixture is then cooled to room temperature, the precipitate is filtered through a paper filter and thoroughly flushed out with water. Next, the crude residue is transferred to a flask and dissolved in 200 ml of water with the addition of 5-6 ml of 25% ammonia. The resulting solution is filtered to remove foreign particles and the filtrate is acidified with an aqueous solution of 5% acetic acid to pH 5. The precipitated residue is separated and discarded, and the filtrate is acidified with HCl to pH 1 and held for 1 hour at 20° C. The precipitated residue is filtered, flushed out with water, then with an alcohol and ether and air dried at room temperature 2.4 g of derivative 4 of the subject substance are obtained in the form of a colorless crystalline powder. The yield is 34% of the theoretical value.

Study of the Biological Activity of the Subject Medicinal Product

Example 1. Determination of Anti-HIV Activity of Derivatives 1-7 of the Subject Medicinal Product Materials and Methods:

Cells. MT-4 human lymphoblastoid cells were used. The cells were incubated in RPMI 1640 medium with 10% serum of cow embryos, 100 µg/ml of gentamicin.

Viruses. HIV-1899A strain was used as the source of the virus.

The drug. Samples of drugs dissolved in dimethylsulfoxide were studied.

Structure of the study:

Study of the cytotoxic effect of the drug.

The investigated medicinal product was added to the cells in various concentrations. The cells were incubated at 37° C. in the atmosphere with 5% of $CO_2$ and at 98% humidity for 5 days. Recording of the results: determination of the viability and the number of the cells by means of a dye.

Study of the antiviral effect of the drug.

The investigated medicinal products were added to the cells at various doses with simultaneous infection with the virus at a dose of 0.01 $TCD_{50}$/cell. The cell cultures were incubated at 37° C. in the atmosphere with 5% of $CO_2$ and at 98% humidity for 5 days. The results were recorded by staining the cells with tetrazolium dye (MTT method) with spectrophotometry and light microscopy: investigation of cytopathic effect of the virus (CPD) and virus-induced formation of syncytium (syncytium is a conglomerate of several cells with a common cell membrane formed as a result of fusion of their membranes).

The degree of protection of cells from the cyto-destructive effect of the virus was determined by the following formula:

$$\text{protection \%} = \frac{A - B}{K - B} \times 100,$$

where

A is the number of viable cells in the experimental group;

B is the same in the infected culture (virus control);

K is the same in the uninfected culture (cell control).

The results of the study are presented in Table 6.

Example 2. Determination of a 50% Lethal Dose of a Mixture of Derivatives 1+2+4 of the Subject Substance ($LD_{50}$) with a Parenteral (Injectable) Mode of Administration Determination of acute toxicity indicators in parenteral mode of administration included experiments in mice weighing 18-20 g, age 8-9 weeks.

In the experiments on rodents, groups of 5 animals of the same sex were used to study each dose. The preparations were dissolved in sterile $H_2O$ and injected into the tail vein (IV).

Results: $LD_{50}$ of a mixture of derivatives 1+2+4 was 2000 to 2500 mg/kg.

Example 3. Determination of $LD_{50}$ of a Mixture of Derivatives 1+2+5 in Enteral Mode of Administration Determination of $LD_{50}$ of the subject substance in the enteral mode of administration.

Determination of acute toxicity indicators in enteral mode of administration included experiments in mice weighing 18-20 g, age 8-9 weeks.

In the experiments on rodents, groups of 5 animals of the same sex were used to study each dose. The drugs were administered intragastrically (IG) in increasing doses according to Litchfield-Wilcoxon method. To do this, they were diluted in 1% starch mucus and the resulting suspension was administered to the animals.

Results: $LD_{50}$ of a mixture of 1+2+5 derivatives was 12000-16000 mg/kg.

Example 4. Determination of $LD_{50}$ in Intravaginal Mode of Administration

Determination of acute toxicity indicators in intravaginal mode of administration included experiments in rats weighing 150-170 g, age 3-3.5 months. Suppositories containing 1000 µg/suppository No.14 were cut with a razor into strips of a smaller size, convenient for vaginal administration. The drug was administered for 12 hours at intervals of 2 hours. The total dosage received by the animal upon administration was 2200 µg/kg. None of the animals showed death and any signs of adverse effects of the drug. The dynamics of body weight in all groups remained normal.

Example 5. Joint Action of the Subject Medicament and Preparations Used to Treat Diseases Caused by Human Immunodeficiency Viruses Materials and Methods:

MT-4 human lymphoblastoid cells were used. The cells were cultured in RPMI 1640 medium with 10% serum of cow embryos, 100 µg/ml gentamicin.

The strain of HIV-$1_{899A}$ was used as a source of the virus.

The drug. Samples of drugs dissolved in dimethylsulfoxide were studied. As an antiretroviral reference drug, Raltegravir (prototype) was used.

Study of the antiviral action of the drug (cell protection).

The investigated drugs were added to the cells at various doses with simultaneous infection with the virus at a dose of 0.01 $TCD_{50}$/cell. Cell cultures were incubated at 37° C. in the atmosphere with 5% $CO_2$ and 98% humidity for 5 days. The results were recorded by staining the cells with tetrazolium dye (MTT method) with spectrophotometry and light microscopy: investigation of cytopathic effect of the virus (CPD) and virus-induced formation of syncytium (syncytium is a conglomerate of several cells with a common cell membrane formed as a result of fusion of their membranes).

The results are given in Table 8.

Thus, it can be concluded that the subject drug has a synergistic effect when used in combination with drugs used to treat diseases caused by human immunodeficiency virus.

Example 6. Effect of the Subject Compounds on the Reproduction of the Hepatitis B Virus (HBV)

Materials and Methods.

HepG2.2.15 line cells infected with Hepatitis B virus were grown in DMEM medium supplemented with 10% bovine serum at 5% $CO_2$, 37° C.

Analysis of the amount of extracellular HBV of the DNA.

After 5 days of HepG2.2.15 incubation the culture medium was selected, the cells were separated by centrifugation, and the DNA was isolated by the Klintschar and Neuhuber method (Klintschar and Neuhuber, 2000). Quantitation of HBV was performed using RT-PCR.

The results are given in Table 9.

The data obtained indicate that the subject drug is active against the hepatitis B virus.

INDUSTRIAL APPLICABILITY

The invention is implemented using common materials and equipment, resulting, according to the applicant's opinion, in compliance of the invention with the "Industrial Applicability" ("IA") patentability criterion.

TABLE 2

The yield and properties of derivatives 1-7 of the subject substance

| Substance | Yield, % | Melting point (dec.), ° C. |
|---|---|---|
| 1 | 40 | 260 (with decomp.) |
| 2 | 19 | 220 (dec.) |
| 3 | 27 | 265-267 |
| 4 | 34 | 270 (with decomp.) |
| 5 | 44 | 260 (with decomp.) |
| 6 | 39 | 244 (with decomp.) |
| 7 | 28 | 265 (with decomp.) |

TABLE 3

The data of proton magnetic resonance spectroscopy of the subject substances 1-7 (DMSO-$d_6$, δ, ppm, J, Hz)

| No. | C(5)H (c, 1H) | ArH (J 8.0-8.2) | OH, br. C (OMe, c, 3H), |
|---|---|---|---|
| 1 | 5.02 | 7.54 (d, 2H), 8.08 (d, 2H) | 12.45 (2H) |
| 2 | 4.87 | 7.65 (d, 2H), 8.12 (d, 2H) | 12.41 (1H), 13.38 (1H) |
| 3 | 5.27 | 7.69 (d, 2H), 8.10 (d, 2H) | 12.91 (1H) |
| 4 | 4.85 | 7.54 (d, 2H), 8.07 (d, 2H) | 12.05 (1H), 13.22 (1H) |
| 5 | 4.82 | 6.54 (m, 1H), 7.56 (m, 2H), 7.97 (d, 2H) | 12.40 (2H) |
| 6 | 4.88 | 6.69 (d, 1H), 7.17 (m, 1H), 7.99 (m, 2H) | 12.42 (2H) |
| 7 | 4.73 | 7.12 (d, 2H), 7.70 (d, 2H) | 12.45 (2H), 3.91 (3H, OMe) |

TABLE 4

Data of elemental analysis of the subject substances

| | Found, % | | | | | Calculated, % | | | |
|---|---|---|---|---|---|---|---|---|---|
| No. | C | H | N | Hal | Gross formula | C | H | N | Hal |
| 1 | 44.01 | 1.79 | 17.05 | 17.11 | $C_{15}H_7Cl_2N_5O_5$ | 44.14 | 1.73 | 17.16 | 17.37 |
| 2 | 44.13 | 2.10 | 17.09 | 8.60 | $C_{15}H_8ClN_5O_4S$ | 44.40 | 1.99 | 17.26 | 8.74 |
| 3 | 42.03 | 1.49 | 16.22 | 24.70 | $C_{15}H_6Cl_3N_5O_4$ | 42.23 | 1.42 | 16.42 | 24.93 |
| 4 | 46.04 | 2.15 | 17.88 | 8.96 | $C_{15}H_8ClN_5O_6$ | 46.23 | 2.07 | 17.97 | 9.10 |
| 5 | 49.47 | 2.34 | 15.25 | 19.30 | $C_{15}H_8Cl_2N_4O_3$ | 49.61 | 2.22 | 15.43 | 19.52 |
| 6 | 45.15 | 1.88 | 13.87 | 26.66 | $C_{15}H_7Cl_3N_4O_3$ | 45.31 | 1.77 | 14.09 | 26.75 |
| 7 | 48.70 | 2.69 | 14.13 | 17.89 | $C_{16}H_{10}Cl_2N_4O_4$ | 48.88 | 2.56 | 14.25 | 18.03 |

TABLE 1

The structure of the most active derivatives of the general formula of the subject drug

| Derivative | X | R1 | R2 |
|---|---|---|---|
| 1 | 4-$NO_2$ | OH | Cl |
| 2 | 4-$NO_2$ | OH | SH |
| 3 | 4-$NO_2$ | Cl | Cl |
| 4 | 4-$NO_2$ | OH | OH |
| 5 | H | OH | Cl |
| 6 | 3-Cl | OH | Cl |
| 7 | 4-OMe | OH | Cl |

TABLE 5

Investigation of antiviral activity on a model of cells infected with HIV-1

| The investigated derivatives in comparison with the prototype and control | Concentration (μg/ml) | Without virus (cytotoxicity) Viability of cells, % | HIV 1 infection | |
|---|---|---|---|---|
| | | | Cytopathic effect of the virus, % | Protection of cells, % |
| 1 | 10 | 100.0 | 0.0-0.0 | 100 |
| | 30 | 100.0 | 0.0-0.0 | 90 |
| | 50 | 100.0 | 0.0-0.0 | 100 |

TABLE 5-continued

Investigation of antiviral activity on a model of cells infected with HIV-1

| The investigated derivatives in comparison with the prototype and control | Concentration (μg/ml) | Without virus (cytotoxicity) Viability of cells, % | HIV 1 infection Cytopathic effect of the virus, % | Protection of cells, % |
|---|---|---|---|---|
| 2 | 10 | 100.0 | 0.0-0.0 | 100 |
|   | 30 | 100.0 | 96-100 | 0 |
|   | 50 | 100.0 | 55-80 | 10 |
| 3 | 10 | 100.0 | 15-70 | 50 |
|   | 30 | 100.0 | 18-92 | 30 |
|   | 50 | 100.0 | 10-40 | 65 |
| 4 | 10 | 100.0 | 0.0-0.0 | 95 |
|   | 30 | 100.0 | 15-60 | 50 |
|   | 50 | 100.0 | 0.0-0.0 | 90 |
| 5 | 10 | 100.0 | 0.0-0.0 | 100 |
|   | 30 | 100.0 | 57.5-80.0 | 10.7 |
|   | 50 | 100.0 | 37.5-62.5 | 71.7 |
| 6 | 10 | 100.0 | 57.5-80.0 | 10.7 |
|   | 30 | 100.0 | 37.5-62.5 | 71.7 |
|   | 50 | 100.0 | 0.0-0.0 | 90.5 |
| 7 | 10 | 100.0 | 12-65 | 45 |
|   | 30 | 100.0 | 5-15 | 80 |
|   | 50 | 100.0 | 0.0-0.0 | 100 |
| 1 + 2 + 4 | 10 | 100.0 | 15-70 | 50 |
|   | 30 | 100.0 | 0.0-0.0 | 100 |
|   | 50 | 100.0 | 0.0-0.0 | 100 |
| Prototype | 10 | 100.0 | 0.0-0.0 | 90 |
|   | 30 | 100.0 | 0.0-0.0 | 100 |
|   | 50 | 100.0 | 0.0 | — |
| Cell control |  | 100.0 | 37.5-100.0 | — |
| Virus control |  | 100.0 | 0.0-0.0 | 90 |

TABLE 6

Determination of $LD_{50}$ of the mixture of derivatives 1 + 2 + 4.

| Dose of the drug (mg/kg) | Number of live animals in the group | Number of dead animals in the group |
|---|---|---|
| 0 | 5 | 0 |
| 250 | 5 | 0 |
| 500 | 5 | 0 |
| 1000 | 5 | 0 |
| 1500 | 5 | 0 |
| 2000 | 5 | 2 |
| 2500 | 5 | 3 |
| 3000 | 5 | 3 |
| 4000 | 5 | 5 |
| 5000 | 5 | 5 |

TABLE 7

Determination of $LD_{50}$ of the mixture of derivatives 1 + 2 + 5.

| Dose of the drug (mg/kg) | Number of live animals in the group | Number of dead animals in the group |
|---|---|---|
| 0 | 5 | 0 |
| 500 | 5 | 0 |
| 1000 | 5 | 0 |
| 2000 | 5 | 0 |
| 4000 | 5 | 0 |
| 6000 | 5 | 0 |
| 8000 | 5 | 0 |
| 12000 | 5 | 2 |
| 16000 | 5 | 2 |
| 24000 | 5 | 5 |

TABLE 8

| Sample | Concentration (μg/ml) | Protection of cells, % |
|---|---|---|
| 1 | 2 | 3 |
| Reverse transcriptase inhibitor (RTI) - Retrovir | 0.003 μg/ml | 13 |
| Derivative 1 + RTI | 5 μg/ml + 0.003 μg/ml | 22 |
| Derivative 2 + RTI | 5 μg/ml + 0.003 μg/ml | 19 |
| Derivative 3 + RTI | 5 μg/ml + 0.003 μg/ml | 18 |
| Derivative 4 + RTI | 5 μg/ml + 0.003 μg/ml | 19 |
| Derivative 5 + RTI | 5 μg/ml + 0.003 μg/ml | 18 |
| Derivative 6 + RTI | 5 μg/ml + 0.003 μg/ml | 21 |
| Derivative 7 + RTI | 5 μg/ml + 0.003 μg/ml | 22 |
| Raltegravir (R) | 10 μg/ml | 23 |
| Derivative 1 + R | 5 μg/ml + 10 μg/ml | 100 |
| Derivative 2 + R | 5 μg/ml + 10 μg/ml | 100 |
| Derivative 7 + R | 5 μg/ml + 10 μg/ml | 100 |
| Protease inhibitor Lopinavir (LPV) | 2.5 μg/ml | 17 |
| Derivative 1 + LPV | 5 μg/ml + 2.5 μg/ml | 100 |
| Derivative 6 + LPV | 5 μg/ml + 2.5 μg/ml | 100 |
| Derivative 7 + LPV | 5 μg/ml + 2.5 μg/ml | 100 |

TABLE 9

The change in the amount of extracellular DNA HBV

| Sample | HBV Log10 IU/ml |
|---|---|
| Control (untreated cells) | 4.42 +/− 0.28 |
| Derivative 1, 5 μg/ml | 2.58 +/− 0.33 |
| Derivative 2, 5 μg/ml | 2.65 +/− 0.19 |
| Derivative 7, 5 μg/ml | 2.74 +/− 0.25 |

The invention claimed is:

1. A pharmaceutical composition comprising:
   (i) at least one compound according to formula (I):

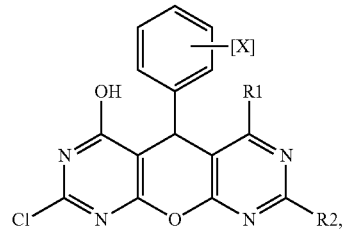

wherein X is selected from H, $NO_2$, Hal, and OMe;
R1 is selected from Cl, and OH;
R2 is selected from Cl, SH, and OH,
or a pharmaceutically acceptable salt thereof,
   (ii) a reverse transcriptase inhibitor, and/or a protease inhibitor, and/or an integrase inhibitor, and
   (iii) a pharmaceutically acceptable carrier or excipient.

2. The pharmaceutical composition of claim 1, wherein the reverse transcriptase inhibitor is Retrovir.

3. The pharmaceutical composition of claim 1, wherein the protease inhibitor is Lopinavir.

4. The pharmaceutical composition of claim 1, wherein the composition is formulated for injection or in the form of a suppository.

5. A method of treating a viral infection in a patient in need thereof, wherein the viral infection is selected from HIV infection and hepatitis B infection, said method comprising administering to said patient a therapeutically effective amount of the composition of claim 1.

6. The pharmaceutical composition of claim 1, wherein in the compound of formula (I) R1 is OH.

7. The pharmaceutical composition of claim 1, wherein in the compound of formula (I) X is 4-NO$_2$ and R1 is OH.

8. The pharmaceutical composition of claim 1, wherein in the compound of formula (I) X is 4-NO$_2$, R1 is OH, and R2 is Cl.

9. The pharmaceutical composition of claim 1, wherein in the compound of formula (I) X is 4-NO$_2$ and R1 is Cl.

10. The pharmaceutical composition of claim 1, wherein in the compound of formula (I) X is selected from H, 3-Cl, and 4-OMe and R1 is OH.

11. The pharmaceutical composition of claim 1 comprising two or more different compounds of formula (I).

12. The pharmaceutical composition of claim 1 comprising three different compounds of formula (I).

13. The pharmaceutical composition of claim 1, wherein one of the compounds is

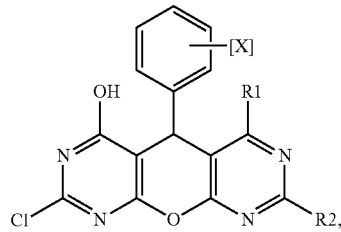

wherein X is 4-NO$_2$, R1 is OH, and R2 is Cl, or a pharmaceutically acceptable salt thereof.

14. The pharmaceutical composition of claim 1, wherein the compound of formula (I) is produced by a method comprising the steps of:
a) combining 2-thiobarbituric acid and a benzaldehyde of formula

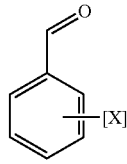

in the presence of a base to obtain an intermediate of formula

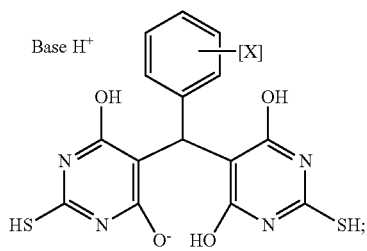

b) combining the intermediate of step (a) with phosphorus oxychloride;
c) pouring the mixture into ice, adding water, and collecting a formed precipitate, and
d) adding an acid to a solution of the precipitate of step (c) to obtain the compound of formula (I).

15. The pharmaceutical composition of claim 1, wherein in the compound of formula (I) X is 4-NO$_2$.

16. A method of treating a viral infection in a patient in need thereof, wherein the viral infection is selected from HIV infection and hepatitis B infection, said method comprising administering to said patient a therapeutically effective amount of a compound according to formula (I):

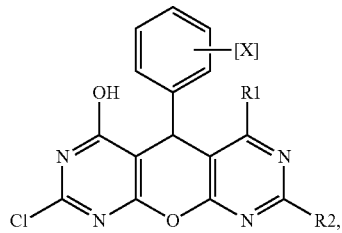

wherein X is selected from H, NO$_2$, Hal, and OMe;
R1 is selected from Cl, and OH;
R2 is selected from Cl, SH, and OH,
or a pharmaceutically acceptable salt thereof.

17. The method of claim 16, wherein the method further comprises administering a reverse transcriptase inhibitor and/or a protease inhibitor.

18. The method of claim 5, wherein the composition is administered intravenously or vaginally.

19. The method of claim 16, wherein the compound is administered intravenously or vaginally.

20. The method of claim 16, wherein in the compound of formula (I) X is 4-NO$_2$.

21. The method of claim 16, wherein in the compound of formula (I) R1 is OH.

22. The method of claim 16, wherein in the compound of formula (I) X is 4-NO$_2$ and R1 is OH.

23. The method of claim 16, wherein in the compound of formula (I) X is 4-NO$_2$, R1 is OH, and R2 is Cl.

24. The method of claim 16, wherein in the compound of formula (I) X is 4-NO$_2$ and R1 is Cl.

25. The method of claim 16, wherein in the compound of formula (I) X is selected from H, 3-Cl, and 4-OMe and R1 is OH.

26. The method of claim 16, wherein the compound of formula (I) is

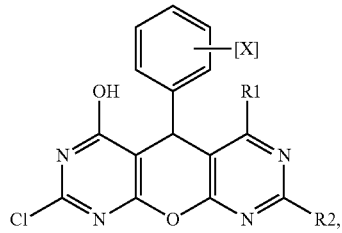

wherein X is 4-NO$_2$, R1 is OH, and R2 is Cl, or a pharmaceutically acceptable salt thereof.

* * * * *